(12) United States Patent
Colb et al.

(10) Patent No.: US 7,449,183 B2
(45) Date of Patent: *Nov. 11, 2008

(54) ENDOTHELIALIZATION OF VASCULAR SURFACES

(76) Inventors: A. Mark Colb, 226 Wren St., West Roxbury, MA (US) 02132; Herman K. Gold, 22 Hyslop Rd., Brookline, MA (US) 02445

(*) Notice: Subject to any disclaimer, the term of this patent is extended or adjusted under 35 U.S.C. 154(b) by 0 days.

This patent is subject to a terminal disclaimer.

(21) Appl. No.: 11/654,770

(22) Filed: Jan. 18, 2007

(65) Prior Publication Data

US 2007/0134235 A1    Jun. 14, 2007

Related U.S. Application Data

(62) Division of application No. 10/353,384, filed on Jan. 29, 2003, now Pat. No. 7,172,758.

(60) Provisional application No. 60/352,684, filed on Jan. 29, 2002.

(51) Int. Cl.
*A61K 39/395* (2006.01)
*A61F 2/00* (2006.01)
*C12P 21/08* (2006.01)
*C07K 16/28* (2006.01)
*C07K 16/44* (2006.01)

(52) U.S. Cl. .................... 424/136.1; 424/422; 424/423; 435/7.1; 530/387.3; 530/388.7

(58) Field of Classification Search ............. 424/136.1, 424/178.1; 530/387.3, 391; 435/325; 623/1.41, 623/23.76, 907
See application file for complete search history.

(56) References Cited

U.S. PATENT DOCUMENTS 7,172,758 B2 *   2/2007   Colb et al. ............... 424/136.1

* cited by examiner

*Primary Examiner*—Phuong Huynh
(74) *Attorney, Agent, or Firm*—Kriegsman & Kriegsman

(57) ABSTRACT

Endothelialization of vascular surfaces. According to one aspect, the invention involves a technique for re-endothelializing an artery whose endothelial layer has been damaged by balloon angioplasty. The technique comprises, in one embodiment, introducing into the bloodstream of a patient, prior to performing the angioplasty, a quantity of a bispecific antibody, the bispecific antibody having a first antigen binding site directed against a surface marker common to both endothelial progenitor cells (EPCs) and endothelial cells (ECs) and having a second antigen binding site directed against a subendothelial epitope. The bispecific antibody is introduced in a quantity sufficient to bind a substantial percentage of circulating EPCs and circulating ECs. In this manner, once the angioplasty has been performed and the target epitopes on the subendothelium have been exposed, the bispecific antibodies that have already become bound to the circulating EPCs and ECs also then bind to the subendothelium. Thus seeded by the bound EPCs and ECs, the exposed subendothelium is covered after a short period of proliferation and differentiation.

6 Claims, 9 Drawing Sheets

ENDOTHELIALIZATION OF VASCULAR SURFACES

CROSS-REFERENCE TO RELATED APPLICATIONS

The present application is a divisional of U.S. patent application Ser. No. 10/353,384, inventors A. Mark Colb and Herman K. Gold, filed Jan. 29, 2003, now U.S. Pat. No. 7,172, 758, which, in turn, claims the benefit under 35 U.S.C. 119(e) of U.S. Provisional Patent Application Ser. No. 60/352,684, filed Jan. 29, 2002, in the names of A. Mark Colb and Herman K. Gold, both of the above-identified patent applications being incorporated herein by reference.

BACKGROUND OF THE INVENTION

The present application relates generally to the treatment of arterial atherosclerotic disease and relates more particularly to techniques for reducing the occurrence of occlusions following treatment for arterial atherosclerotic disease.

Atherosclerosis, which involves the deposition of a fatty plaque on the luminal surface of an artery, is one of the leading causes of death and disability in the world. This is because the deposition of plaque on the luminal surface of an artery causes a narrowing of the cross-sectional area of the artery. Such a narrowing reduces or effectively blocks blood flow distal to the site of the narrowing, causing ischemic damage to those tissues supplied by the artery.

A coronary artery is an artery that supplies the heart with blood. Consequently, a narrowing of the coronary artery lumen comprises the perfusion of heart muscle. This results in angina with exertion or even at rest. A complete occlusion of a vessel results in myocardial infarction, often causing death or subsequent heart failure. Unfortunately, the problem of coronary artherosclerosis is pervasive. There are well over 1.5 million myocardial infarctions in the United States each year. Acute myocardial infarctions result each year in the deaths of hundreds of thousands.

The preferred treatment for coronary atherosclerosis is percutaneous transluminal coronary balloon angioplasty ("PTCA"), with approximately one million such procedures performed each year in the United States alone. In PTCA, a balloon catheter is percutaneously inserted into a peripheral artery and is then threaded through the arterial system into the narrowed coronary artery. The balloon is then inflated so as to expand radially outwardly, thereby flattening the fatty plaque within the narrowed artery against the arterial wall and increasing the cross-sectional flow of blood through the treated coronary artery. Unfortunately, approximately 30-40% of those patients who undergo PTCA suffer from restenosis or a re-narrowing of the treated artery within six months of the procedure.

This restenosis is a response to local injury of the vessel wall by the balloon. Mechanisms of restenosis include (i) constrictive remodeling, likely due to retractile scar formation within the arterial wall, and (ii) the proliferation of smooth muscle cells with accompanying synthesis of extracellular matrix. This proliferation occurs in the intima, the layer beneath the inner lining of endothelial cells. (This endothelium is stripped by the angioplasty.) The resulting thickening of the intimal layer (neointima) re-narrows the artery. See e.g., Van Belle et al., "Endothelial regrowth after arterial injury: from vascular repair to therapeutics,"*Cardiovascular Research,* 38(1): 54-68 (April, 1998), which is incorporated herein by reference.

A number of different approaches have been devised to deal with the problem of post-angioplasty restenosis, including treating the patient with various drugs (see e.g., Lefkovits et al., *Progress in Cardiovascular Diseases,* 40(2):141-58 (September/October, 1997), which is incorporated herein by reference), administering radiation to the angioplasty site to inhibit neointimal thickening (see e.g., Coussement et al., *Circulation,* 104:2459-64 (2001), which is incorporated herein by reference) or, more successfully, implanting a stent in the artery at the affected site. A stent is a scaffold typically in the form of a tubular metal mesh that is used to mechanically keep an artery open. Although the use of stents has reduced the rate of restenosis to about 20-30%, there is obviously much room for improvement. Moreover, it appears that while stents reduce the risk of restenosis by eliminating constrictive remodeling, stents do not inhibit neointimal proliferation. See e.g., Leon et al., "Localized Intracoronary Gamma-Radiation Therapy to Inhibit the Recurrence of Restenosis After Stenting," *N. Eng. J. Med.,* 344(4): 250-6 (Jan. 25, 2001); and Farb et al., "Pathology of Acute and Chronic Coronary Stenting in Humans," *Circulation,* 99:44-52 (1999); both of which are incorporated herein by reference. In fact, a repeat angioplasty performed on a re-narrowed lesion within a stent has an even higher rate of restenosis—approaching 50%.

Drug-coated stents releasing cytotoxic agents, such as paclitaxel and sirolimus, have shown promising results in relatively short periods of follow-up. However, the long-term outlook for this approach remains unknown at present. In animal models, benefits are shown to be short-lived. See Virmani et al., *Herz,* 27:1-6 (2002), which is incorporated herein by reference.

In view of the above, it can be readily appreciated that there is a definite need for a technique for minimizing, over the long-term, the occurrence of restenosis in coronary arteries following balloon angioplasty. To accomplish this, it is necessary to prevent or to reduce the proliferation of smooth muscle cells in the neointima, as described above. There is evidence from various animal models that an intact endothelial lining does suppress cell proliferation in the intimal layer beneath. (Van Belle et al., cited above). Furthermore, in experimental models of angioplasty, the local delivery by catheter of endothelial growth factors accelerates endothelial resurfacing and concurrently inhibits intimal hyperplasia. (See Asahara et al., *Circulation,* 91:2793-801 (1995) and Yasuda et al., *Circulation,* 101:2546-9 (2000), both of which are incorporated herein by reference.) Therefore, rapid re-endothelialization is widely regarded as an important objective in reducing restenosis. Nevertheless, despite evidence suggesting the desirability of rapid re-endothelialization following angioplasty, an effective means for achieving this objective has not heretofore been provided. By contrast, the natural re-endothelialization of an area of angioplasty takes many weeks, which is far too long to effectively inhibit restenosis. Such natural re-endothelialization is thought to occur principally through the ingrowth of endothelial cells from the edges of the treated area and from the orifices of any small branch arteries within the area of angioplasty.

It should be noted that the narrowing of an artery due to atherosclerosis is not limited to the coronary arteries, but can occur in all other arteries as well. Clinically important sites of disease include the carotid, aortoiliac, superficial femoral, profunda femoris, popliteal, tibial, subclavian and mesenteric arteries. Peripheral vascular disease, i.e., atherosclerotic disease in an artery of the lower limbs, can be treated with a modicum of success using percutaneous transluminal balloon angioplasty (preferably followed by the implantation into the treated artery of a stent). However, the preferred and more successful treatment involves bypassing the narrowed section of the artery using a tubular graft. Such a graft is typically either an autologous venous segment or a synthetic graft. In the case of a synthetic graft, the graft is typically made of polyethylene terephthalate (PET, Dacron) or polytetrafluoroethylene (PTFE) and is additionally often impregnated with a biomolecule, such as collagen, to reduce the microporosity of the graft.

As can be readily appreciated, an autologous venous segment suitable for use as a graft is often unavailable in patients suffering from atherosclerosis. This may be due to venous disease or to prior use in other vascular surgery. Accordingly, the use of a synthetic graft is necessary in many cases. Unfortunately, however, thrombosis or clotting is a very significant problem for synthetic grafts, resulting in low long-term patency rates for synthetic bypass grafts—especially when such grafts are placed below the groin. For example, the five-year patency rate for synthetic grafts placed below the groin and above the knee is approximately 50% (open) and for grafts placed below the knee is approximately 15% (open).

Endothelial cells are the natural lining of blood vessels. These cells produce TPA and other molecules that inhibit thrombosis. It is widely accepted that the development of an endothelial cell lining on the surface of a synthetic graft may prevent thrombosis therewithin. Unfortunately, however, no practical method has yet been devised for forming such a layer of endothelial cells on a synthetic graft. Clinical studies of the effects of endothelialization on graft patency have depended on harvesting endothelial cells from the patient (e.g., from an excised vein), growing them in tissue culture, and then seeding them onto the graft before surgery. See e.g., Laube et al., *The Journal of Thoracic and Cardiovascular Surgery*, 120(1):134-41 (July, 2000); Deutsch et al., *Surgery*, 126(5):847-55 (November, 1999); Fujita et al., *Ann. Vasc. Surg.*, 13(4):402-12 (1999); Salacinski et al., *Med. Biol. Eng. Comput.*, 39:609-18 (2001); Ozaki et al., *J. Vasc. Surg.*, 18:486-94 (1993); Carr et al., *Ann. Vasc. Surg.*, 10:469-75 (1996); Vinard et al., *Ann. Vasc. Surg.*, 13:141-50 (1999); and Bhattacharya et al., *Blood*, 95(2):581-5 (15 Jan. 2000), all of which are incorporated herein by reference. The seeded graft is then implanted into the patient.

As can readily be appreciated, the approach described above is most demanding, laborious, and time-consuming and is not at all suitable for general use. Nevertheless, the benefits of graft endothelialization have been demonstrated. For instance, in the study by Deutsch et al. cited above, the 9-year patency rate was 65% for endothelialized infrainguinal (below groin) grafts compared with 16% patency in the control group.

In U.S. Patent Application Publication No. US 2002/0049495, which was published Apr. 25, 2002, and which is incorporated herein by reference, there is disclosed a coating composition that is applied in the production of a medical device, such as a stent or a synthetic graft, to promote the adherence of endothelial cells to the medical device. According to said published patent application, the coating composition comprises a matrix incorporating monospecific antibodies reactive with endothelial cells. The matrix may be composed of a synthetic material, such as fullerenes, polyurethane, poly-L-lactic acid, cellulose ester or polyethylene glycol, or may be composed of a naturally occurring material, such as collagen, fibrin, elastin or amorphous carbon. The matrix may comprise several layers, with a first layer being composed of synthetic or naturally occurring materials and a second layer composed of antibodies. The matrix may be covalently or non-covalently attached to the medical device, with the antibodies being covalently attached to the matrix using hetero- or homobifunctional cross-linking reagents. To bind endothelial cells to the thus-coated medical device, the coated medical device is incubated in the presence of endothelial cells.

The present inventors have noted certain significant shortcomings with the technique of the aforementioned published patent application. First, to the extent that the subject published patent application teaches using a coated stent, by itself, to seed endothelialization, such an approach will likely be insufficient because a stent, which is a wire mesh, covers only a very small percentage of a denuded arterial surface and, therefore, provides only a minimal surface area for the attachment of cells.

In addition, because a deployed stent recoils outwardly, pressing against its surrounding arterial wall, the struts of the stent are effectively buried in furrows of the luminal surface, even breaking through that surface in many cases. As a result, the stent struts are not well enough exposed to blood in the lumen for efficient capture of endothelial cells from the blood.

Insofar as the above-mentioned published patent application relates to synthetic grafts, the technique specified therein also suffers from the shortcoming that it requires that currently commercially available graft materials first be modified by the application thereto of an antibody—containing coating matrix in order to be made ready for endothelialization. In other words, such a technique does not permit the endothelialization of off-the-shelf graft materials as they are.

An additional concern of the technique described in the subject published patent application relates to the efficacy of the antibody incorporated into the coating matrix applied to the medical device. These antibody molecules may be sterically constrained by noncovalent interactions with other matrix components so that their antigen binding sites are not freely available for binding cells in the blood.

SUMMARY OF THE INVENTION

It is an object of the present invention to provide a novel technique for minimizing the occurrence of restenosis in an artery, such as a coronary artery, following the performing of a balloon angioplasty on said artery.

It is another object of the present invention to provide a technique as described above that overcomes at least some of the shortcomings associated with existing techniques for minimizing the occurrence of restenosis in an artery following balloon angioplasty.

In accordance with the teachings of the present invention, said technique involves re-endothelializing the artery whose endothelial layer has been removed by a balloon angioplasty. This may be done, according to a first embodiment, by introducing into the bloodstream of the patient a quantity of a multispecific antibody, said multispecific antibody comprising a first antigen binding site and a second antigen binding site, said first antigen binding site being directed against a surface marker of endothelial progenitor cells (EPCs) (and preferably being directed against a surface marker common to both endothelial progenitor cells (EPCs) and endothelial cells (ECs)), said second antigen binding site being directed against a subendothelial epitope. The multispecific antibody is preferably introduced into the bloodstream just prior to the performance of the angioplasty and is introduced in a quantity sufficient to bind a high percentage of circulating endothelial progenitor cells (and, where the surface marker is common to both EPCs and ECs, circulating endothelial cells as well). In this manner, once the angioplasty has been performed and the target epitopes on the subendothelium have been exposed, the multispecific antibodies that have bound the circulating EPCs (and, where applicable, ECs as well) then bind these cells to the subendothelium. Thus seeded by the bound EPCs (and, where applicable, ECs as well), the exposed subendothelium is covered after a short period of proliferation and differentiation.

According to a second embodiment of the technique, instead of introducing a multispecific antibody into the bloodstream of the patient, one introduces into the bloodstream of the patient a first antibody directed against a surface marker of endothelial progenitor cells (said surface marker preferably also being a surface marker of endothelial cells) and a second antibody directed against a subendothelial epitope, one of said first antibody and said second antibody being conjugated to avidin, the other of said first antibody and said second antibody being conjugated to biotin. Preferably, the first antibody is introduced into the bloodstream prior to the performance of the angioplasty, and the second antibody is introduced into the bloodstream at the time of the angioplasty or soon thereafter. In this manner, the first antibody binds to the circulating EPCs (and, preferably, to the circulating ECs as well), and then the second antibody binds to the exposed subendothelium, with the first and second antibodies thereafter binding to one another via their respective avidin and biotin moieties.

According to a third embodiment of the technique, a stent or like medical device, prior to being implanted within an artery on which angioplasty is performed, is coated with a compound against which a first antigen binding site of a multispecific antibody is directed, a second antigen binding site of the multispecific antibody being directed against a surface marker of endothelial progenitor cells (said surface marker preferably also being a surface marker of endothelial cells). The multispecific antibody is preferably introduced into the bloodstream just prior to the performance of the angioplasty (and the subsequent implanting of the stent). Preferably, the compound coated onto the stent is also present in the exposed subendothelium so that the multispecific antibody promotes adherence of EPCs (and, where applicable, ECs as well) onto both the exposed subendothelium and the stent. Alternatively, the compound coated onto the stent may not be present in the exposed subendothelium, and a plurality of different multispecific antibodies are introduced into the bloodstream of the patient, one such multispecific antibody being used to mediate the binding of the EPCs (and, where applicable, ECs as well) to the stent, the other multispecific antibody being used to mediate the binding of the EPCs (and, where applicable, ECs as well) to the exposed subendothelium. Alternatively, instead of using a plurality of different multispecific antibodies, one could replace the multispecific antibody that is used to mediate the binding of the EPCs (and, where applicable, ECs as well) to the stent with an antibody directed against the endothelial progenitor cell surface marker, said antibody being conjugated to one of avidin and biotin, the stent being coated with the other of avidin and biotin. As another alternative, one could replace the multispecific antibody that is used to mediate the binding of the EPCs (and, where applicable, ECs as well) to the stent with a first antibody and a second antibody, the first antibody being directed against an endothelial progenitor cell surface marker and being conjugated to one of avidin and biotin, the second antibody being directed against the compound coated onto the stent and being conjugated to the other of avidin and biotin. Preferably, the first antibody is introduced into the bloodstream prior to the performing of the angioplasty (and the subsequent implanting of the stent), and the second antibody is introduced into the bloodstream at the time the stent is implanted or soon thereafter.

The present invention is also directed to a novel technique for endothelializing a synthetic vascular graft or other like intravascular medical device. In so doing, the incidence of thrombosis within the implanted graft or medical device may be reduced.

According to a first embodiment of said technique, the synthetic graft is impregnated, during its manufacture, with an antigenic substance, such as collagen. A quantity of a multispecific antibody is introduced into the bloodstream of the patient, said multispecific antibody comprising a first antigen binding site and a second antigen binding site, said first antigen binding site being directed against a surface marker of an endothelial progenitor cell (said surface marker preferably also being a surface marker of endothelial cells), said second antigen binding site being directed against the antigenic substance with which the synthetic graft has been impregnated. The multispecific antibody is preferably introduced into the bloodstream just prior to the implanting of the synthetic graft and is introduced in a quantity sufficient to bind a high percentage of circulating EPCs (and, where applicable, circulating ECs as well). In this manner, once the synthetic graft has been implanted, the multispecific antibodies that have already bound to the circulating EPCs (and, where applicable, ECs as well) also then bind these cells to the synthetic graft. Thus seeded by the bound EPCs (and, where applicable, ECs as well), the graft becomes covered by a monolayer of endothelial cells after a short period of proliferation and differentiation.

According to a second embodiment of said technique, the multispecific antibody is applied to the impregnated synthetic graft prior to implantation of the graft into the patient. This may be done, for example, by incubating the graft in a solution containing the multispecific antibody. When the graft is then implanted into a patient, the multispecific antibody that has already become bound to the graft then also binds circulating EPCs (and, where applicable, ECs as well) causing their adherence to the graft.

According to a third embodiment of said technique, the multispecific antibody used to mediate the binding of EPCs (and, where applicable, ECs) onto the graft is replaced with a first antibody and a second antibody, the first antibody being directed against a surface marker of endothelial progenitor cells (said surface marker preferably also being a surface marker of endothelial cells) and being conjugated to one of avidin and biotin, the second antibody being directed against the compound impregnated into the graft and being conjugated to the other of avidin and biotin. Preferably, the first antibody is introduced into the bloodstream prior to the implanting of the graft, and the second antibody is introduced into the bloodstream at the time the graft is implanted or soon thereafter.

According to a fourth embodiment of said technique, the synthetic graft is conjugated, prior to implantation, with one of avidin and biotin, and the multispecific antibody is replaced with an antibody directed against a surface marker of endothelial progenitor cells (said surface marker preferably also being a surface marker of endothelial cells), said antibody being conjugated with the other of avidin and biotin. The antibody is preferably introduced into the bloodstream of the patient just prior to the implanting of the synthetic graft and is introduced in a quantity sufficient to bind a high percentage of circulating EPCs (and, where applicable, circulating ECs as well). In this manner, once the synthetic graft has been implanted, the antibodies that have already become bound to the circulating EPCs (and, where applicable, ECs as well) also then bind to the synthetic graft through the avidin-biotin mechanism. Alternatively, instead of introducing the conjugated antibody to the patient prior to the implanting of the conjugated synthetic graft, the conjugated synthetic graft may be incubated in a solution containing the conjugated antibody. In this manner, the conjugated antibody is bound to the graft prior to the graft being implanted in the patient. Following the implantation of the graft in the patient, the graft-bound antibody binds the circulating EPCs (and, where applicable ECs as well), mediating their capture onto the graft.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference characters represent like parts.

DETAILED DESCRIPTION OF PREFERRED EMBODIMENTS

The present invention is directed to a novel technique for endothelializing vascular surfaces, both natural and synthetic. One application of the technique is in the re-endothelialization of an arterial segment whose endothelial layer has been removed, for example, as a result of a balloon angioplasty. Such a re-endothelialization of the damaged artery using the present technique is expected to reduce the occurrence of restenosis therein. Another application of the technique is in the endothelialization of a synthetic vascular graft of the type used, for example, to bypass or replace a blocked arterial segment. The endothelialization of such a graft using the present technique is expected to reduce the occurrence of thrombosis therein.

The present invention exploits a potential endothelial layer repair mechanism that already exists in the form of circulating endothelial progenitor cells (EPCs) and, to a lesser extent, endothelial cells (ECs). (Mature endothelial cells (ECs) also circulate, though in much lower numbers. Lin et al., *J. Clin. Invest.*, 105:71-7 (2000), which is incorporated herein by reference. ECs are able to proliferate and can also be incorporated at sites of injury.) EPCs are known to incorporate into very small blood vessels being actively formed at sites of wound healing, ischemia and tumor growth. (See Asahara et al., *Circ. Res.*, 85:221-8 (1999), which is incorporated herein by reference.) However, EPCs clearly incorporate very inefficiently at sites of angioplasty and hardly at all in synthetic grafts. The fact that an efficient mechanism does not exist physiologically for patching EPCs into the bare surface of an artery while under arterial pressure is not surprising, given that extensive areas of nude arterial surface in need of endothelialiazation, as occur in angioplasties and synthetic grafts, do not arise naturally. It has, however, been shown that an increase in the number of circulating EPCs and in their adhesiveness results in improved EPC incorporation and faster re-endothelialization. (See Walter et al., *Circulation*, 105: 3017-24 (2002), which is incorporated herein by reference.)

The present invention effectively shortens the time required for re-endothelialization (and, in so doing, reduces the likelihood of neointimal thickening) by using antibodies to increase dramatically the efficiency at which circulating EPCs (and, preferably, ECs as well) are seeded onto sites of bare arterial wall.

According to a first embodiment, this acceleration of EPC (or, preferably, both EPC and EC) seeding is accomplished by introducing into the bloodstream of a patient, e.g., by injection, a quantity of a multispecific antibody, said multispecific antibody comprising a first antigen binding site and a second antigen binding site, said first antigen binding site being directed against a surface marker of endothelial progenitor cells (said surface marker preferably also being a surface marker of endothelial cells), said second antigen binding site being directed against a subendothelial epitope. The multispecific antibody is preferably introduced into the bloodstream just prior to performance of the angioplasty (but may also be introduced during or after the angioplasty) and is introduced in a quantity sufficient to bind a high percentage of circulating EPCs (and, preferably, circulating ECs as well). In this manner, once the angioplasty has been performed and the target epitopes on the subendothelium have been exposed, the multispecific antibodies that have already become bound to the circulating EPCs (and, preferably, ECs as well) also then bind to the subendothelium. Thus seeded by the bound EPCs (and, preferably, ECs as well), the exposed subendothelium is covered after a short period of proliferation and differentiation.

If desired, instead of using a multispecific antibody having a first antigen binding site that binds a surface marker common to both EPCs and ECs, one could use different types of multi specific antibodies, one such type of multispecific antibody having a first antigen binding site that is specific to EPCs, another such type of multispecific antibody having a first antigen binding site that is specific to ECs. The second antigen binding site of such multispecific antibodies may be directed to a common subendothelial epitope.

Figure 1A:
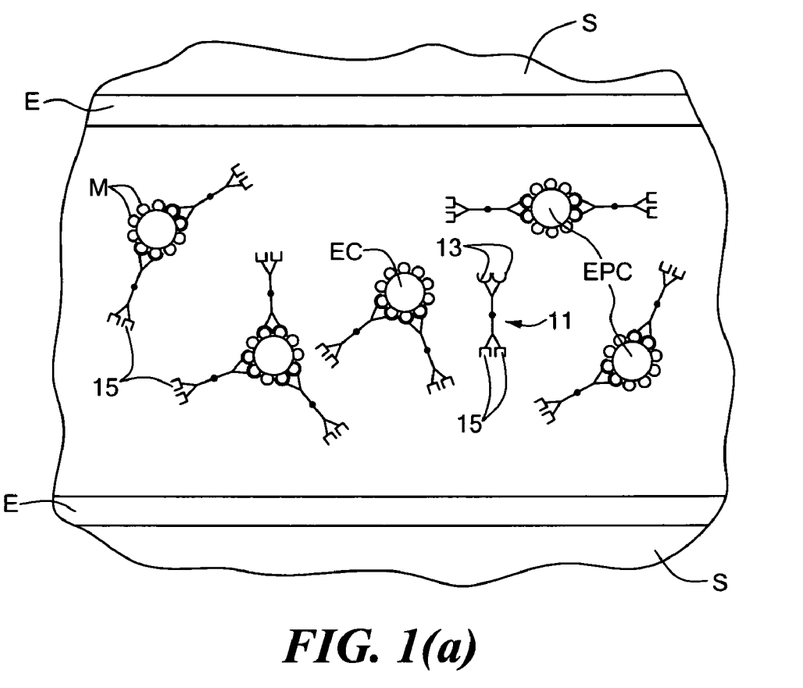
FIGS. 1(a) through 1(c) are schematic views illustrating the re-endothelialization of an artery using a bispecific antibody in accordance with the teachings of the present invention.
Figure 1B:
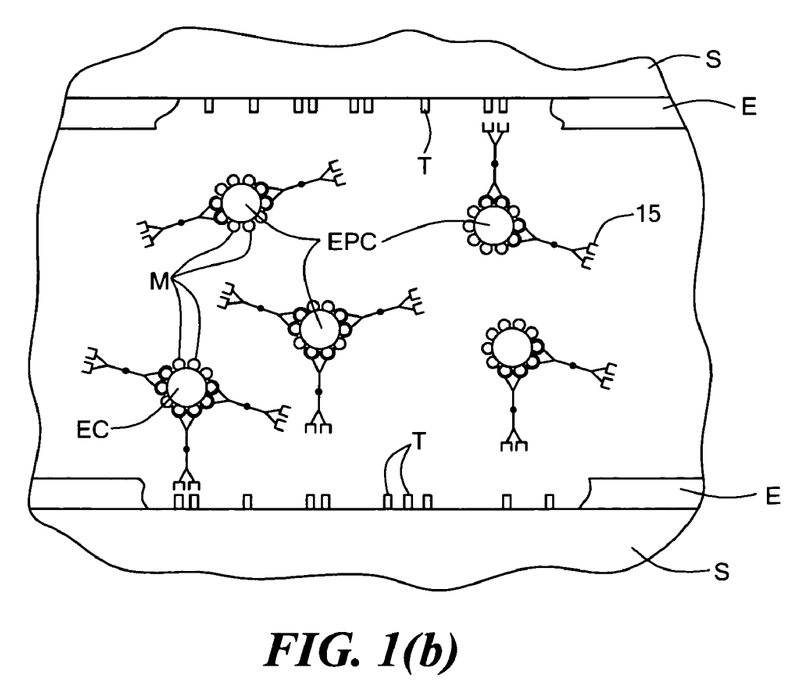
Figure 1C:
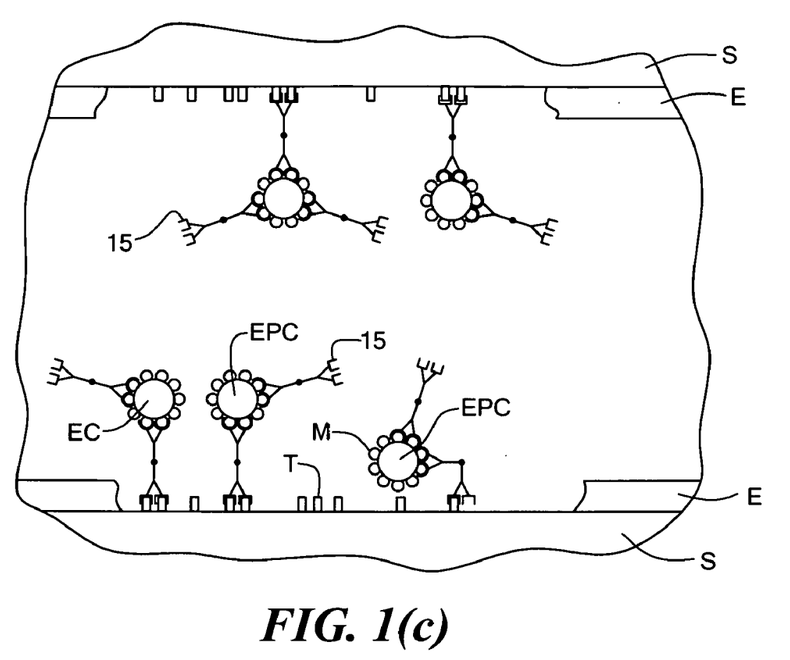

Referring now to FIGS. 1(a) through 1(c), there is shown a series of schematic views illustrating generally the re-endothelialization technique described above. In FIG. 1(a), prior to an angioplasty being performed to flatten the plaque (not shown) deposited against the endothelial layer E of an artery, a quantity of a bispecific antibody 11 is injected into a patient's bloodstream, each such bispecific antibody 11 comprising a pair of first antigen binding sites 13 and a pair of second antigen binding sites 15, said bispecific antibodies 11 binding via their first antigen binding sites 13 to surface markers M common to both circulating endothelial progenitor cells EPCs and circulating endothelial cells ECs. In FIG. 1(b), as a result of the angioplasty being performed, a portion of the endothelial layer E of the artery is stripped, exposing target epitopes T in the subendothelial matrix S. In FIG. 1(c), the bispecific antibodies 11, which are already bound to the endothelial progenitor cells EPCs and to the endothelial cells ECs, bind to the target epitopes T through their second antigen binding sites 15, thereby seeding the endothelial progenitor cells EPCs and endothelial cells ECs onto the subendothelium.

The present inventors believe that the foregoing technique will permit re-endothelialization within a time frame sufficient to minimize neointimal thickening. Although not wishing to be limited to any particular theory or explanation as to how the invention operates, the present inventors offer the following: Two independent scientific studies (Kalka et al., *PNAS*, 97(7):3422-7 (2000); and Peichev et al., *Blood*, 95(3): 952-8 (2000), both of which are incorporated herein by reference) have determined that EPCs constitute about 0.02-0.05% of the total peripheral blood mononuclear cells (PBMNCs). Since the count of PBMNCs is normally in the range of $1-5 \times 10^6$/ml, the number of circulating EPCs is in the range of several hundred to several thousand per ml. We will then assume, for the sake of discussion, that the number of circulating EPCs is 1000/ml. We will also assume, for the sake of discussion, that the multispecific antibody mediates a capture rate of 0.1% per centimeter of bare artery. That is, one in a thousand EPCs are trapped as they pass a one centimeter length of vessel, or 1 EPC/ml of flow. With a typical flow rate in a coronary artery after angioplasty of 100 ml per minute, it is reasonable to assume that 100 EPCs are trapped per minute per centimeter. After 24 hours, approximately 150,000 EPCs will be trapped. At confluence, the density of an endothelial monolayer is $\sim 10^5$ cells/cm$^2$. Therefore, 150,000 EPCs are sufficient to line a vessel of 5 mm diameter for a length of 1 cm (area $\sim 1.5$ cm$^2$). Allowing time for limited additional proliferation and for differentiation, the resurfacing should be complete in 1-2 weeks. Even if the capture rate is an order of magnitude lower, that is $10^{-4}$, and three additional doublings are required after one day's capture of EPCs, the resurfacing should still be much accelerated. We expect that this rapid coverage with endothelial cells will inhibit intimal hyperplasia and restenosis.

Examples of suitable endothelial progenitor cell (EPC) surface markers against which the first antigen binding site of the aforementioned multispecific antibody may be directed include AC133, CD34, and VEGFR-2. Examples of suitable endothelial cell (EC) surface markers against which the first antigen binding site of the aforementioned multispecific antibody may be directed include CD146, CD34, and VEGFR-2. See e.g., Asahara et al., *Science*, 275:964-7 (1997); Reyes et al., *J. Clin. Invest.*, 109:337-46 (2002); Gehling et al., *Blood*, 95(10):3106-12 (2000); Brugger et al., *Blood*, 84(5):1421-6 (1994); Quirici et al., *Brit. J. Haemat.*, 115:186-94 (2001); Vasa et al., *Circulation*, 103:2885-90 (2001); Shi et al., *Blood*, 92(2):362-7 (1998); and Kawamoto et al., *Circulation*, 103: 634-7 (2001), all of which are incorporated herein by reference. These markers are highly, but not absolutely, specific. AC133 and CD34, markers of EPCs, are also present on the surface of hematopoietic stem cells, but not on any differentiated blood cells. The incidental capture of hematopoietic stem cells along with the desired EPCs onto the vascular surface being seeded should not interfere in any way with the intended re-endothelialization. In fact, it has been shown in dogs that the complete CD34+ fraction, seeded onto graft surfaces ex vivo, does accelerate endothelialization after graft implantation. (See Bhattacharya et al., *Blood*, 95:581-5 (2000), which is incorporated herein by reference.)

Examples of suitable subendothelial components against which the second antigen binding site may be directed include collagen (especially types 1 and 3), elastin, laminin, and fibronectin. The interior of a plaque is rich in collagen and other proteinaceous components of connective tissue matrix. (Virmani et al., *ARTERIOSCLER THROMB VASC BIOL*, 20:1262-75 (2000), which is incorporated herein by reference.) Hence, the exposed interior can be targeted along with subendothelium by the same antigen binding site. (The typical angioplasty exposes both subendothelium and plaque interior.)

Fibrin may also be a suitable target for the second antigen binding site in certain situations. Fibrin deposition may persist, for instance, over stented areas or graft surfaces as the residue of clotting. Therefore, it may be possible to re-endothelialize grafts or stents placed months before by targeting fibrin.

Multispecific antibodies for use in the above-described technique may be prepared, for example, by any means known in the art including, but not limited to, those techniques disclosed in U.S. Pat. Nos. 6,458,933; 4,714,681; 4,444,878; and 4,331,647, as well as in Wickham et al., *J. Virol.*, 70(10):6831-8 (1996), all of which are incorporated herein by reference. Such multispecific antibodies may comprise two or more intact antibodies that are covalently bound to one another or may comprise two or more antibody fragments, e.g., Fab, F(ab')$_2$, F$_v$, that are covalently bound to one another. For purposes of the present specification and claims, the term "antibody," unless specifically limited otherwise, shall be construed broadly enough to encompass any molecule containing an antigen-binding site derived from an antibody, either directly or through subcloning a DNA fragment encoding the site. Each antibody fragment of the subject multispecific antibody may be monovalent (i.e., containing one antigen binding site) or multivalent (i.e., containing a plurality of antigen binding sites). Each such antibody fragment may have a similar or dissimilar valence to another such antibody fragment. Components of the multispecific antibody may be prepared from monoclonal antibodies or from polyclonal antibodies. Fragments may be derived from specific digestion (e.g., with papain or pepsin), reductive cleavage of disulfide bonds, or by other treatment of antibody molecules, methods for which are well-established. Fragments may also be derived through subcloning of DNA fragments encoding the antigen binding site into appropriate vectors that permit expression in prokaryotic or eukaryotic cells. Methods for deriving such fragments are also well-known in the art.

Representative techniques for preparing bispecific antibodies are as follows: Begin with pure preparations of two different monoclonal antibodies (Mab). One Mab is reacted with SATA (N-succinimidyl S-acetylthioacetate). The product is then deprotected by treatment with hydroxylamine to yield an SH-Mab, the antibody now containing free sulfhydryl groups. The second Mab is reacted with sSMCC (sulfosuccinimidyl 4-(N-maleimidomethyl)cyclohexane-1-carboxylate). The respective reactions products SH-Mab and sSMCC-Mab are purified by gel filtration under argon, and then reacted together. The product of this coupling reaction is the desired conjugated bispecific antibody, which is then purified by gel filtration. Details of the procedure are given in Lindorfer et al., *J. Immunol.*, 167:2240-9 (2001), which is incorporated herein by reference.

Digestion of an IgG antibody molecule with pepsin releases an F(ab')$_2$ fragment containing two antigen-binding sites linked by a disulfide bond between the two heavy chains. This bond can be cleaved by reduction releasing two identical Fab', fragments containing the binding sites. These Fab' fragments can be mixed with the Fab' fragments derived from a second Mab, and disulfide linkages then reformed by oxidation. Among the products there will be bispecific F(ab')$_2$ fragments with one Fab from each of the original Mabs. This bispecific product can then be chromatographically purified.

Alternatively, Fab', fragments of one specificity (derived from one Mab) can be activated with an excess of bis-maleimide linker (1,1'-(methylenedi-4,1-phenylene)bis-maleimide). Fab' fragments of a second Mab (released by reduction of F(ab')$_2$ fragments), can then be reacted with the activated Fab' fragments of the first Mab to give a high yield of bispecific molecules.

It is also possible to produce bispecific antibodies through cell fusion of two hybridoma cells secreting the respective Mabs. These so-called hybrid-hybridomas can be selected in culture by standard means, and then screened for the production of both antibodies. Bispecific antibody molecules will be among the secreted products, along with bivalent antibody of the two 'parental' types. The bispecific molecules can then be purified by hydrophobic interaction chromatography. (See Weiner et al., *J. Immunol.*, 147:4035-44 (1991), which is incorporated herein by reference.)

Recombinant DNA technology can also be utilized in the preparation of bispecific antibody fragments. The F$_v$ fragment contains the antigen binding site of the antibody. It consists of the V$_L$ and V$_H$ subfragments in noncovalent association. If a peptide linker is interposed between them covalently, a fusion protein results, known as an SCF$_v$ (single chain variable fragment). The SCF$_v$ can bind the target epitope. DNA encoding an SCF$_v$, or more than one, can be subcloned into a vector that contains all necessary regulatory elements to permit expression in a prokaryotic or a eukaryotic cell. This host cell then produces the desired bispecific molecule.

Certain of these and other established methods are readily adaptable to the preparation of higher order molecules containing additional binding sites for the same two or for additional target epitopes.

The necessary Mabs directed at the various targets identified above, and contributing binding sites to multispecific antibodies, are available. In addition, other Mabs directed at these targets can be readily isolated using methods that are routine in the practice of the art.

As for targets in impregnated synthetic grafts or subendothelium, monoclonals can be isolated so as to ensure binding to the intact structure and not simply to purified components. Lengths of grafts or of denuded artery can be used in the screening by phage display technology. In this way, the isolated clones will recognize target structures as they will appear during treatment, configured and assembled, and not simply in the form of pure components.

To enhance the targeting of the subendothelium, one may use a cocktail of bispecific antibodies differing in their respective second antigen binding sites so as to be directed against different subendothelial connective tissue components. Alternatively, one may use multispecific antibodies having, in addition to one or more endothelial progenitor cell (and, preferably, endothelial cell) binding sites, a plurality of different subendothelial binding sites. Available techniques, cited above, permit the conjugation of multiple fragments, yielding antibody molecules with multiple and diverse binding sites.

According to a second embodiment of the technique, instead of introducing a multispecific antibody into the bloodstream of the patient, one first introduces into the bloodstream of the patient a first antibody directed against an endothelial progenitor cell surface marker (said surface marker preferably also being a surface marker of endothelial cells) and then introduces into the bloodstream of the patient a second antibody directed against a subendothelial epitope, one of said first antibody and said second antibody being conjugated to avidin, the other of said first antibody and said second antibody being conjugated to biotin. Preferably, the first antibody is introduced prior to performance of an angioplasty, and the second antibody is introduced at the time of angioplasty or soon thereafter. In this manner, the first antibody binds to the circulating EPCs (and, preferably, circulating ECs as well), and the second antibody binds to the exposed subendothelium, with the first and second antibodies binding to one another via their respective avidin and biotin moieties. The critical step of cell capture from flowing blood is then mediated by an extremely high affinity interaction, namely, that between avidin and biotin. The dissociation constant (K$_D$) of this binding is $10^{-15}$ M. Methods for biotinylation and avidin conjugation of antibody molecules are very well known in the art.

Figure 2A:
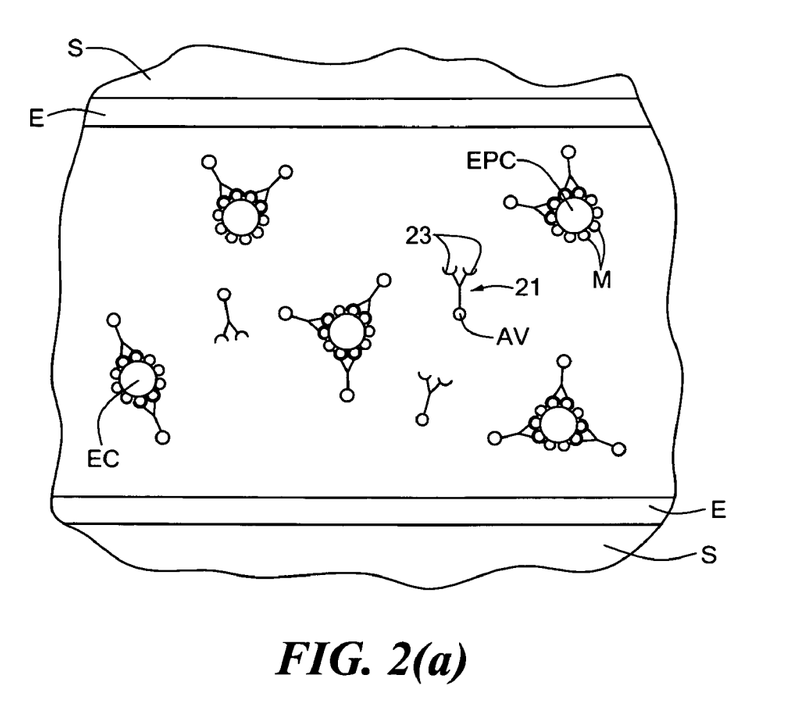
FIGS. 2(a) through 2(c) are schematic views illustrating the re-endothelialization of an artery using a pair of antibodies in accordance with the teachings of the present invention, one of said antibodies being directed against a surface marker common to both endothelial progenitor cells and endothelial cells and being conjugated to biotin, the other of said antibodies being directed against a subendothelial epitope and being conjugated to avidin.
Figure 2B:
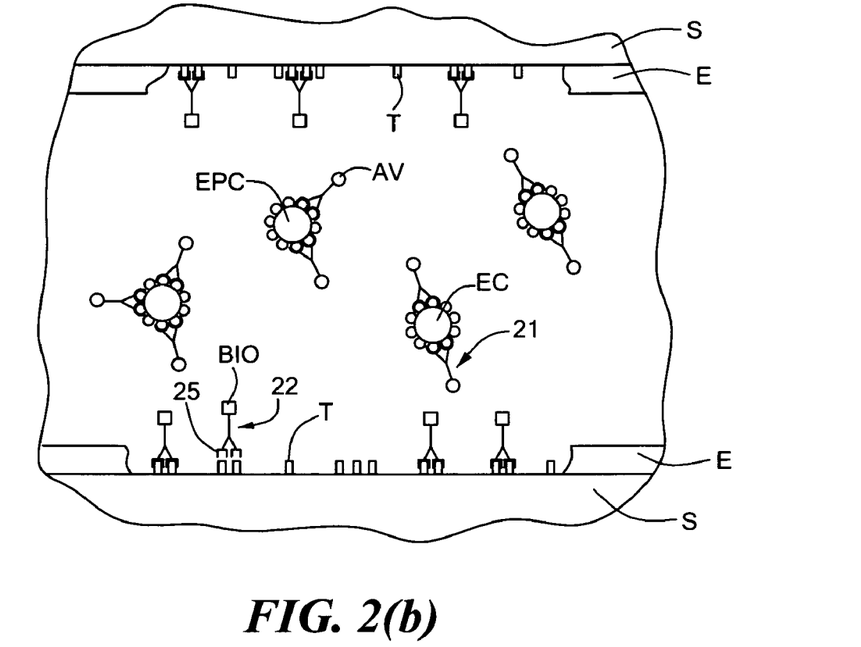
Figure 2C:
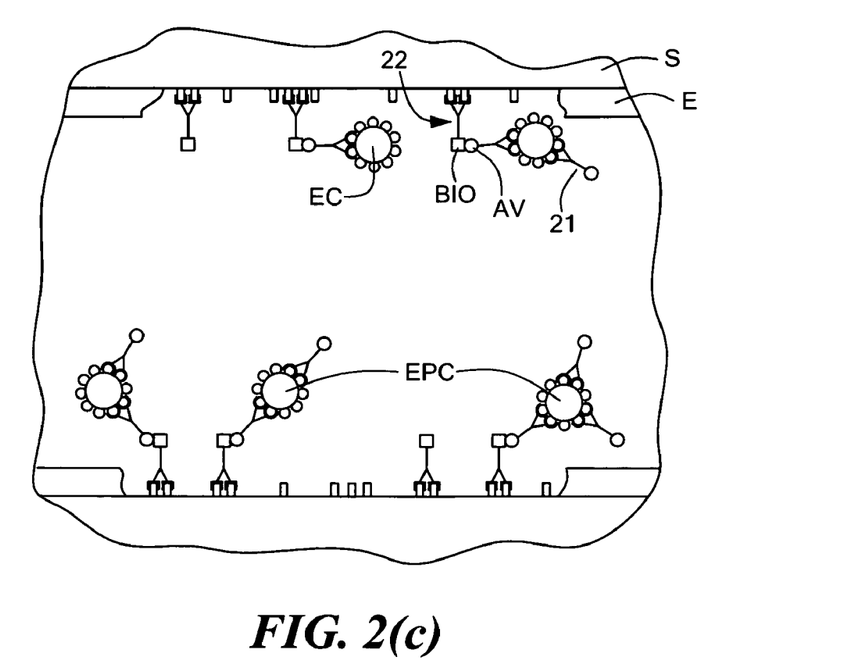

Referring now to FIGS. 2(a) through 2(c), there is shown a series of schematic views illustrating the re-endothelialization technique described above. In FIG. 2(a), prior to an angioplasty being performed to flatten the plaque (not shown) deposited against the endothelial layer E of an artery, an antibody 21 is injected into a patient's bloodstream. Antibody 21, which is conjugated to an avidin moiety AV, comprises a pair of first antigen binding sites 23 adapted to bind to surface markers M present on both circulating endothelial progenitor cells EPCs and circulating endothelial cells ECs. In FIG. 2(b), as a result of the angioplasty being performed, a portion of the endothelial layer E of the artery is stripped, exposing target epitopes T in the subendothelial matrix S. At this time, an antibody 22 is injected into the patent's bloodstream. Antibody 22, which is conjugated to a biotin moiety BIO, comprises a pair of second antigen binding sites 25 adapted to bind to a subendothelial epitope T. As can be seen, antibodies 21 bind to the circulating endothelial progenitor cells EPCs and endothelial cells ECs, and antibodies 22 bind to the subendothelial epitope T. In FIG. 2(c), because of the affinity between avidin and biotin, antibodies 21 and 22 additionally bind to one another through their respective avidin and biotin moieties. (It should be understood that there may be variations in the sequence in which antibodies 21 and 22 are administered and their time relation to angioplasty.)

According to a third embodiment of the technique, a stent or like medical device, prior to being implanted within an artery on which angioplasty is performed, is coated with a compound against which a first antigen binding site of a multispecific antibody is directed, a second antigen binding site of the multispecific antibody being directed against an endothelial progenitor cell surface marker (said surface marker preferably also being a surface marker of endothelial cells). The multispecific antibody is preferably introduced into the bloodstream just prior to the performing of the angioplasty (and the subsequent deployment of the stent). Preferably, the compound coated onto the stent is also present in the exposed subendothelium so that the multispecific antibody promotes adherence of EPCs (and, preferably, ECs as well) onto both the exposed subendothelium and the stent. For example, the compound coated onto the stent may be collagen. Alternatively, the compound coated onto the stent may not be present in the exposed subendothelium, and a plurality of different multispecific antibodies are introduced into the bloodstream of the patient, one such multispecific antibody being used to mediate the binding of the EPCs (and, preferably, ECs as well) to the stent, the other multispecific antibody being used to mediate the binding of the EPCs (and, preferably, ECs as well) to the exposed subendothelium. Alternatively, instead of using a plurality of different multispecific antibodies, one could replace the multispecific antibody that is used to mediate the binding of the EPCs (and, preferably, ECs as well) to the stent with an antibody directed against the endothelial progenitor cell surface marker, said antibody being conjugated to one of avidin and biotin, the stent being coated with the other of avidin and biotin. Methods for coating a stent or like device are known in the art, as exemplified by U.S. Pat. No. 5,925,552, which is incorporated herein by reference, and U.S. Patent Application Publication No. US 2002/0049495, which is discussed above.

As noted above, the present invention is also directed to a novel technique for endothelializing a synthetic vascular graft or other intravascular medical device (e.g., artificial heart, left ventricular assist device, indwelling drug infusion catheter, inferior vena cava filter, etc.). In so doing, the incidence of thrombosis within the implanted graft or medical device may be reduced.

According to a first embodiment of said technique, the synthetic graft is impregnated, prior to implantation, with an antigenic substance, such as collagen. Synthetic vascular grafts impregnated with collagen are presently commercially available, an example being the Hemashield® vascular graft (Meadox Medicals, Inc., Oakland, N.J.). A quantity of a multispecific antibody is introduced into the bloodstream of the patient, said multispecific antibody comprising a first antigen binding site and a second antigen binding site, said first antigen binding site being directed against progenitor cell surface marker (said surface marker preferably also being a surface marker of endothelial cells), said second antigen binding site being directed against the impregnated antigenic substance in the synthetic graft. The multispecific antibody is preferably introduced into the bloodstream just prior to the implanting of the synthetic graft (but may also be introduced during or after the implanting of the graft) and is introduced in a quantity sufficient to bind a high percentage of circulating EPCs (and, preferably, circulating ECs as well). In this manner, once the synthetic graft has been implanted, the multispecific antibodies that have already become bound to the circulating EPCs (and, preferably, ECs as well) also then bind to the synthetic graft. Thus seeded by the bound EPCs (and, preferably, ECs as well), the graft becomes covered by a monolayer of endothelial cells after a short period of proliferation and differentiation.

Figure 3A:
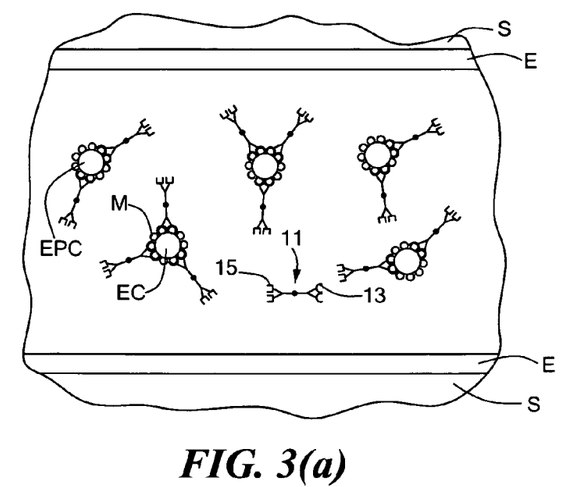
FIGS. 3(a) through 3(c) are schematic views illustrating the endothelialization of a synthetic vascular graft using a bispecific antibody in accordance with one embodiment of the present invention.
Figure 3B:
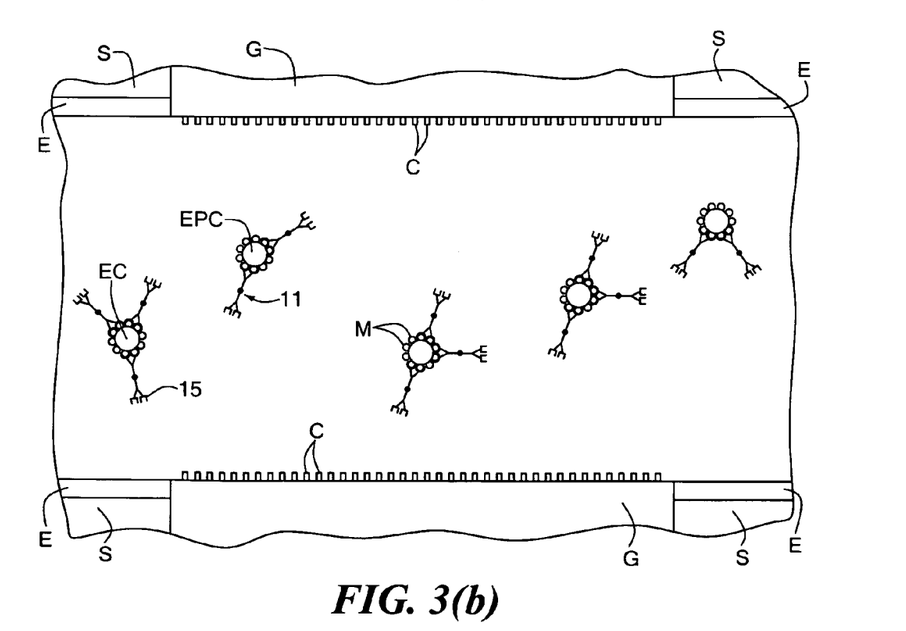
Figure 3C:
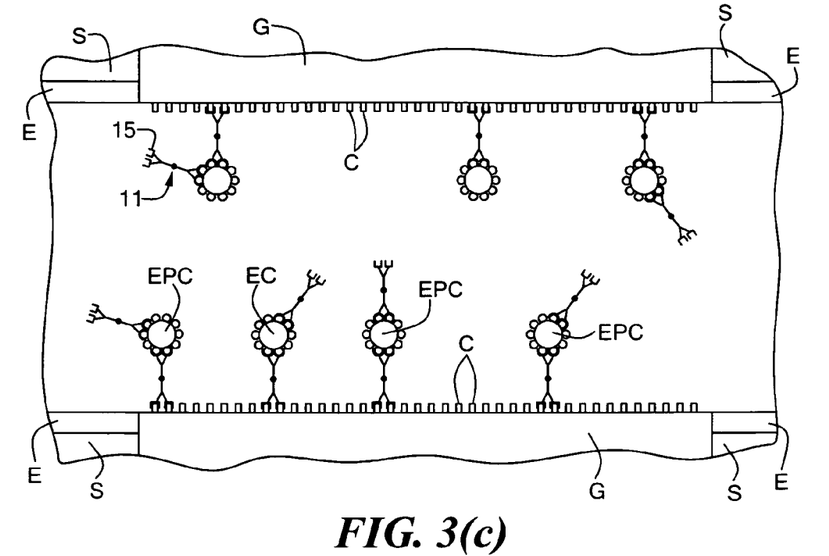

Referring now to FIGS. 3(a) through 3(c), there is shown a series of schematic views illustrating the endothelialization technique described above. In FIG. 3(a), prior to implanting a collagen-impregnated synthetic graft, a quantity of a bispecific antibody 11 is injected into a patient's bloodstream (the plaque in the patient's vessel not being shown), each such bispecific antibody 11 comprising a pair of first antigen binding sites 13 and a pair of second antigen binding sites 15, said bispecific antibodies 11 binding via their first antigen binding sites 13 to surface markers M present on circulating endothelial progenitor cells EPCs and on circulating endothelial cells ECs. In FIG. 3(b), a graft G impregnated with collagen C is implanted in the patient. In FIG. 3(c), the bispecific antibodies 11, which are already bound to the endothelial progenitor cells EPCs and to the endothelial cells ECs, bind to the collagen C in the graft G through their second antigen binding sites 15, thereby seeding the EPCs and ECs onto the graft G.

As can readily be appreciated, by using a synthetic graft of the type that is already impregnated with collagen, for instance, one can implant the graft in the patient unchanged from its commercially available form. Endothelialization of this graft occurs entirely in vivo. Even when such a graft has been implanted long before, the bispecific antibody described above can be administered to endothelialize it. This embodiment applies equally to synthetic grafts impregnated with any other antigenic substance that can serve as a target for a similar bispecific antibody.

According to a second embodiment of said technique, the multispecific antibody is applied to the impregnated synthetic graft prior to implantation of the graft into the patient. This may be done, for example, by incubating the graft in a solution containing the multispecific antibody. When the graft is then implanted into a patient, the multispecific antibody that has already become bound to the graft then also binds circulating EPCs (and, depending on the type of multispecific antibody used, ECs as well).

Figure 4A:
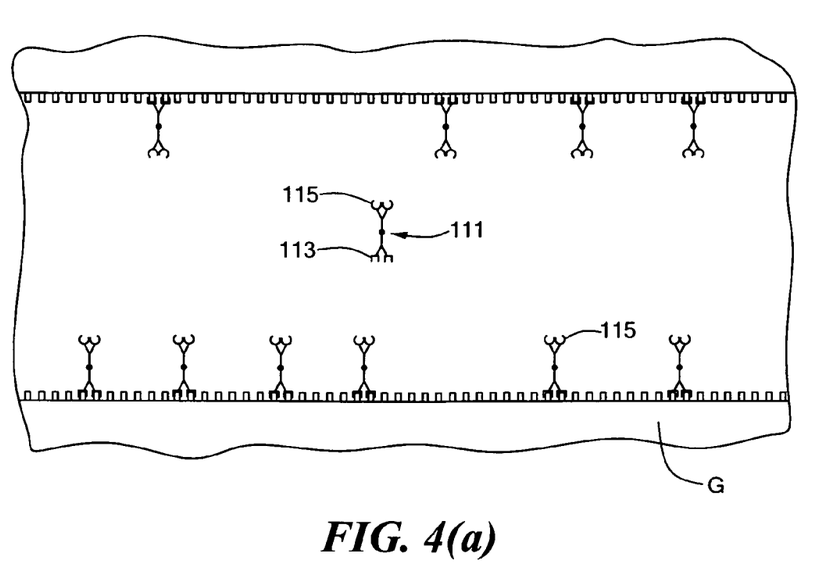
FIGS. 4(a) and 4(b) are schematic views illustrating the endothelialization of a synthetic vascular graft using a bispecific antibody in accordance with another embodiment of the present invention.
Figure 4B:
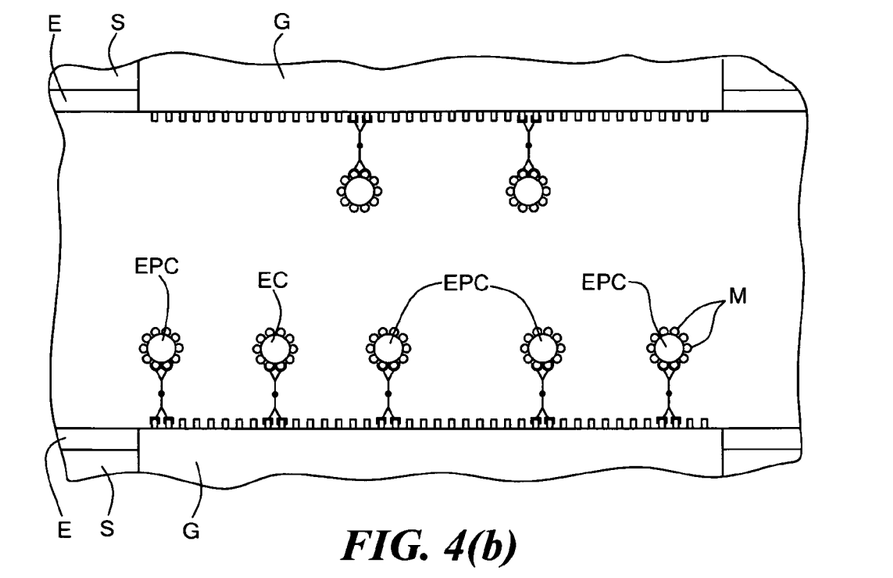

Referring now to FIGS. 4(a) and 4(b), there is shown a series of schematic views illustrating the endothelialization technique described above. In FIG. 4(a), prior to implanting a collagen-impregnated synthetic graft in a patient, the graft G is incubated in a solution containing a quantity of a bispecific antibody 111, bispecific antibody 111 comprising a pair of first antigen binding sites 113 and a pair of second antigen binding sites 115, said bispecific antibodies 111 binding via their first antigen binding sites 113 to the collagen C present on graft G. In FIG. 4(b), the graft G to which antibodies 111 have become bound is then implanted in a patient (graft G replacing an excised blocked arterial segment (not shown)). As can be seen, circulating endothelial progenitor cells EPCs and circulating endothelial cells ECs quickly become bound to antibodies 111 through the interaction of surface markers M on endothelial progenitor cells EPCs and on endothelial cells ECs to second antigen binding sites 115, resulting in the seeding of endothelial progenitor cells EPCs and endothelial cells ECs onto graft G.

According to a third embodiment of said technique, the multispecific antibody is replaced with a first antibody and a second antibody. The first antibody is directed against an endothelial progenitor cell surface marker (said surface marker preferably also being a surface marker of endothelial cells), and the second antibody is directed against a target molecule in the graft, such as collagen. One of the first antibody and the second antibody is conjugated to avidin, the other of said first antibody and said second antibody being conjugated to biotin. Preferably, prior to placement of the graft in the patient, the first antibody is introduced into the bloodstream of the patient, and the graft is incubated in a solution containing the second antibody. Alternatively, instead of incubating the graft in a solution containing the second antibody prior to placement of the graft in the patient, the second antibody may be introduced into the bloodstream of the patient, preferably after placement of the graft in the patient.

Figure 5A:
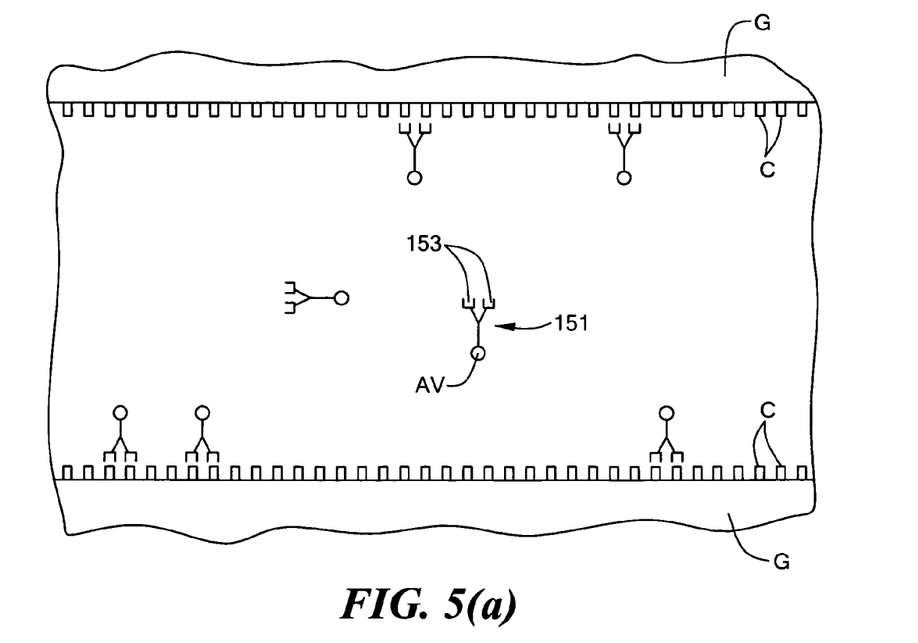
FIG. 5(a) through 5(c) are schematic views illustrating the endothelialization of a synthetic vascular graft impregnated with collagen using an avidin-conjugated antibody directed against said collagen of the synthetic vascular graft and a biotin-conjugated antibody directed to a surface marker common to both endothelial progenitor cells and endothelial cells.
Figure 5B:
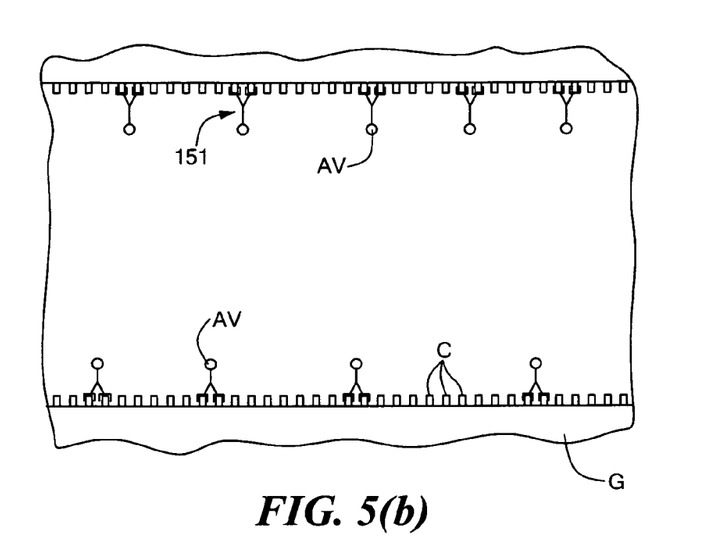
Figure 5C:
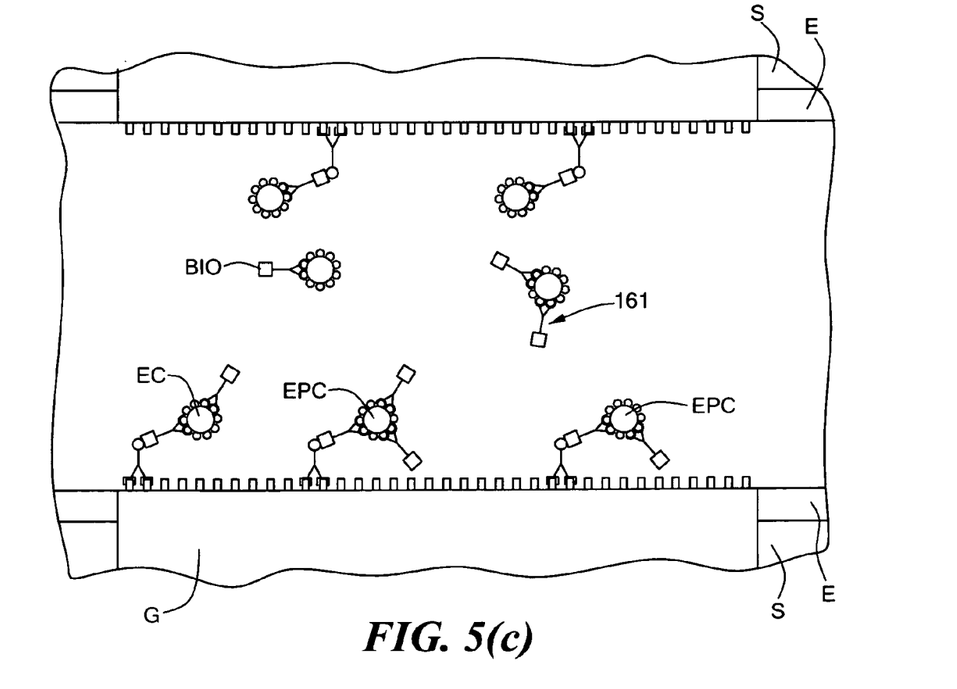

Referring now to FIGS. 5(a) through 5(c), there is shown a series of schematic views illustrating the endothelialization technique described above. In FIG. 5(a), the collagen-impregnated graft G is incubated in a solution containing a quantity of an avidin-conjugated antibody 151, antibody 151 comprising a pair of first antigen binding sites 153 for binding the impregnated collagen C in graft G. In FIG. 5(b), after the passage of time, a quantity of antibody 151 becomes bound to collagen C. In FIG. 5(c), the avidin-complexed graft G is implanted in a patient (graft G replacing an excised blocked arterial segment (not shown)). As can be seen, circulating endothelial progenitor cells EPCs and circulating endothelial cells ECs, which have already become bound to a biotin-conjugated antibody 161 administered prior to graft implantation, quickly become bound to antibodies 151 through the avidin and biotin moieties of antibodies 151 and 161, respectively, resulting in the seeding of endothelial progenitor cells EPCs and endothelial cells ECs onto graft G.

According to a fourth embodiment of said technique, the synthetic graft is impregnated or conjugated, prior to implantation, with one of avidin and biotin, and the multispecific antibody is replaced with an antibody directed against an endothelial progenitor cell surface marker (said surface marker preferably also being a surface marker of endothelial cells), said antibody being conjugated with the other of avidin and biotin. The antibody is preferably introduced into the bloodstream of the patient just prior to the implanting of the synthetic graft and is introduced in a quantity sufficient to bind a high percentage of circulating EPCs (and, preferably, circulating ECs as well). In this manner, once the synthetic graft has been implanted, the antibodies that have already become bound to the circulating EPCs (and, preferably, ECs as well) also then bind to the synthetic graft through the avidin-biotin mechanism. Methods for impregnation of a synthetic graft are known. For instance, see U.S. Pat. No. 5,851, 230, which is incorporated herein by reference. Attachment through linkers is also readily practicable.

Figure 6A:
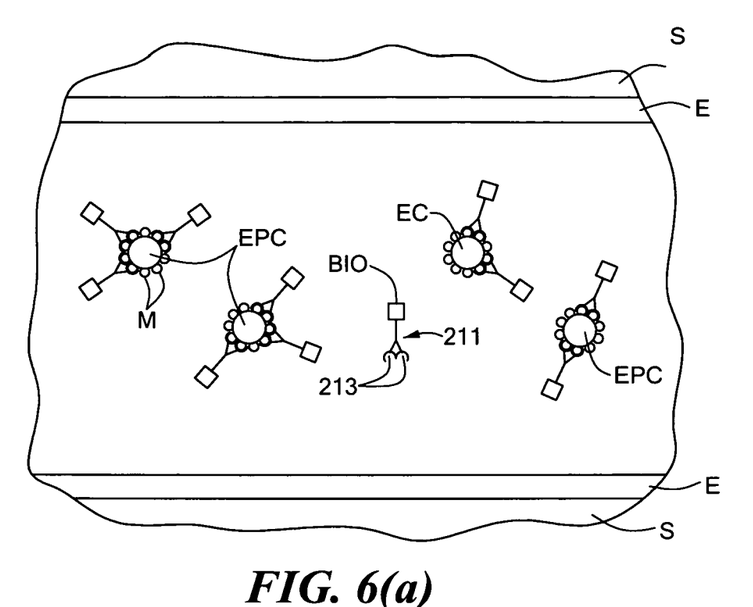
FIG. 6(a) through 6(c) are schematic views illustrating the endothelialization of a synthetic vascular graft impregnated with avidin using a biotin-conjugated antibody directed against a surface marker common to both endothelial progenitor cells and endothelial cells.
Figure 6B:
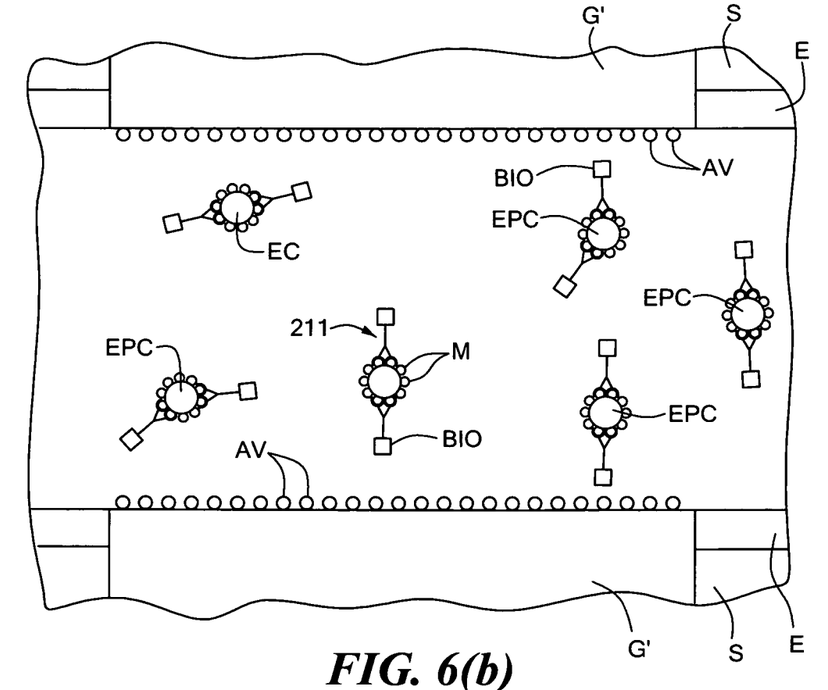
Figure 6C:
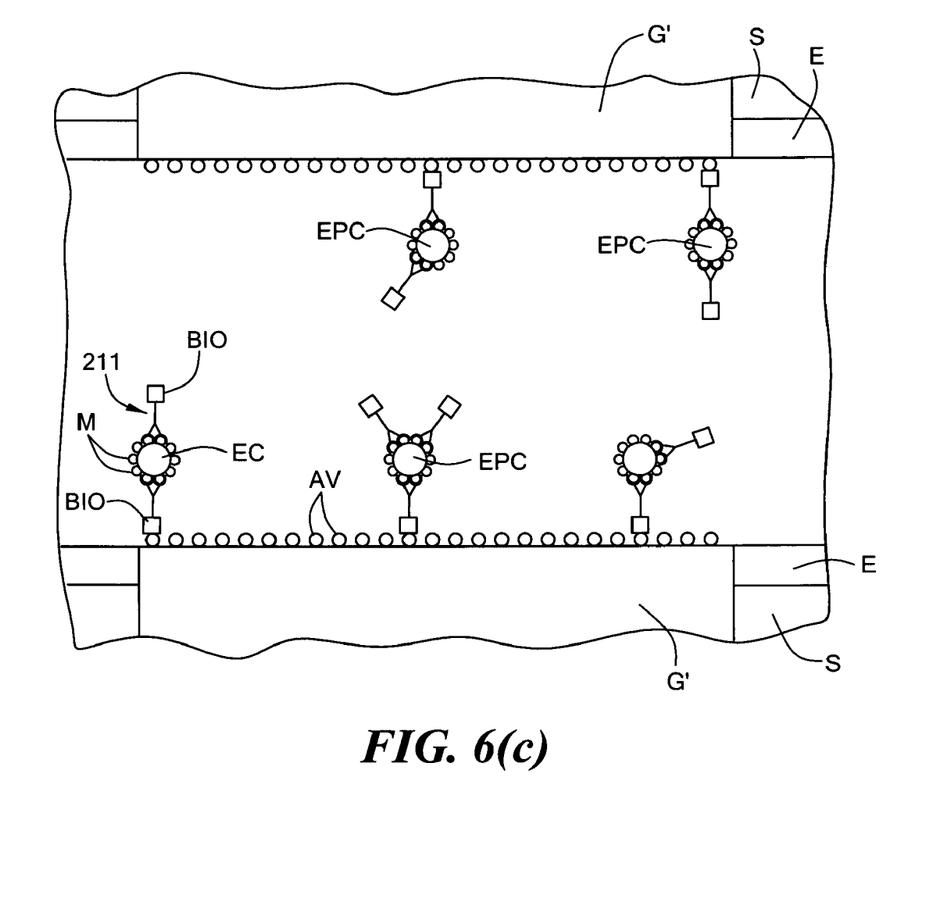

Referring now to FIGS. 6(a) through 6(c), there is shown a series of schematic views illustrating the endothelialization technique described above. In FIG. 6(a), prior to implanting an avidin-impregnated synthetic graft, a quantity of an antibody 211 is injected into a patient's bloodstream (the plaque in the patient's vessel not being shown), antibody 211 being conjugated to biotin BIO and comprising a pair of antigen binding sites 213 for binding surface markers M present on circulating endothelial progenitor cells EPCs and on circulating endothelial cells ECs. In FIG. 6(b), a graft G' impregnated or conjugated with avidin AV is implanted in the patient (graft G' replacing an excised blocked arterial segment (not shown)). In FIG. 6(c), the antibodies 211, which are already bound to the endothelial progenitor cells EPCs and to the endothelial cells ECs, bind to the avidin AV in the graft G' through their biotin BIO moieties, thereby seeding the EPCs and ECs onto the graft G'.

Alternatively, instead of introducing the conjugated antibody into the patient prior to the implanting of the impregnated synthetic graft, the impregnated synthetic graft may be incubated in a solution containing the conjugated antibody. In this manner, the conjugated antibody is bound to the graft prior to the graft being implanted in the patient. Following the implantation of the graft in the patient, the graft-bound antibody binds to the circulating EPCs and Ecs.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for endothelializing a vascular medical device adapted for implantation into a patient, the vascular medical device containing an exposed antigenic collagen, said method comprising the steps of:
    (a) administering to the patient an effective amount of a bispecific antibody, said bispecific antibody comprising a first antigen binding site and a second antigen binding site, said first antigen binding site being directed against a surface marker of an endothelial progenitor cell, said surface marker being CD34, said second antigen binding site being directed against the collagen of the vascular medical device; and
    (b) implanting said vascular medical device in the patient, whereby the binding of said bispecific antibody to the collagen of the vascular medical device and to the CD34 on endothelial progenitor cell resulting in endothelialization of the vascular medical device.

2. The method as claimed in claim 1 wherein the vascular medical device is a synthetic vascular graft and wherein the synthetic vascular graft is coated with collagen.

3. The method as claimed in claim 1 wherein the vascular medical device is a stent and wherein the stent is coated with collagen.

4. A method for endothelializing a vascular medical device adapted for implantation into a patient, the vascular medical device containing an exposed antigenic collagen, said method comprising the steps of:
    (a) incubating said vascular medical device with an effective amount of a bispecific antibody, said bispecific antibody comprising a first antigen binding site and a second antigen binding site, said first antigen binding site being directed against a surface marker of an endothelial progenitor cell, said surface marker being CD34, said second antigen binding site being directed against the collagen of the vascular medical device; and
    (b) then, implanting the vascular medical device of step (a) in the patient, whereby the binding of the bispecific antibody to the collagen of the vascular medical device and to the CD34 on endothelial progenitor cell resulting in endothelialization of the vascular medical device.

5. The method as claimed in claim 4 wherein the vascular medical device is a synthetic vascular graft and wherein the synthetic vascular graft, prior to being incubated with the bispecific antibody of step (a), is coated with collagen.

6. The method as claimed in claim 4 wherein the vascular medical device is a stent and wherein the stent, prior to being incubated with the bispecific antibody of step (a), is coated with collagen.

* * * * *